(12) United States Patent
Thüring et al.

(10) Patent No.: US 12,274,818 B2
(45) Date of Patent: Apr. 15, 2025

(54) BABY BOTTLE WITH BOTTLE TOP ATTACHMENT

(71) Applicant: MEDELA HOLDING AG, Baar (CH)

(72) Inventors: Martin Thüring, Merenschwand (CH); Armin Felber, Lucerne (CH); Mario Rigert, Buchrain (CH)

(73) Assignee: MEDELA HOLDING AG, Baar (CH)

( * ) Notice: Subject to any disclaimer, the term of this patent is extended or adjusted under 35 U.S.C. 154(b) by 0 days.

(21) Appl. No.: 18/210,454

(22) Filed: Jun. 15, 2023

(65) Prior Publication Data

US 2023/0321328 A1 Oct. 12, 2023

Related U.S. Application Data

(63) Continuation of application No. 17/262,648, filed as application No. PCT/EP2019/071744 on Aug. 13, 2019, now abandoned.

(30) Foreign Application Priority Data

Aug. 16, 2018 (EP) ..................................... 18189368

(51) Int. Cl.
*A61M 1/06* (2006.01)
*A61J 9/00* (2006.01)

(52) U.S. Cl.
CPC .................. *A61M 1/06* (2013.01); *A61J 9/00* (2013.01); *A61M 1/062* (2014.02); *A61J 2200/76* (2013.01); *A61M 2205/3389* (2013.01)

(58) Field of Classification Search
CPC ............................................ A61M 1/06–0697
See application file for complete search history.

(56) References Cited

U.S. PATENT DOCUMENTS

| 4,346,596 A | * | 8/1982 | Diamant | ................. G01F 15/08 73/215 |
| 4,820,281 A | | 4/1989 | Lawler, Jr. | |
| 6,673,036 B1 | * | 1/2004 | Britto | ................ A61M 1/06935 604/74 |
| 11,433,166 B2 | | 9/2022 | Analytis et al. | |

(Continued)

FOREIGN PATENT DOCUMENTS

| CN | 1683022 A | 10/2005 |
| CN | 107205356 A | 9/2017 |

(Continued)

OTHER PUBLICATIONS

International Search Report for International Application No. PCT/EP2019/071744, mailed Oct. 17, 2019, with translation.

(Continued)

*Primary Examiner* — Courtney B Fredrickson
(74) *Attorney, Agent, or Firm* — MARSHALL, GERSTEIN & BORUN LLP

(57) ABSTRACT

An apparatus comprising a baby bottle (2) and a bottle top attachment (4) coupled to the baby bottle (2) and having a connector (6) for a breast pump. The apparatus is characterized in that the bottle top attachment (4) includes a measuring head (8) with a reservoir (10) for breast milk and in that the measuring head (8) includes a sensor unit that is associated with the volume of the reservoir (10) and that enables determining a parameter of the milk expressed into the baby bottle.

13 Claims, 3 Drawing Sheets

(56) References Cited

U.S. PATENT DOCUMENTS

| | | | |
|---|---|---|---|
| 2005/0228342 A1* | 10/2005 | Yuen | A61M 1/0697 |
| | | | 604/74 |
| 2008/0154202 A1 | 6/2008 | Nemoto et al. | |
| 2014/0288422 A1 | 9/2014 | Brady et al. | |
| 2015/0051458 A1 | 2/2015 | Chen et al. | |
| 2015/0065994 A1 | 3/2015 | Fridman et al. | |
| 2015/0283311 A1 | 10/2015 | Alvarez et al. | |
| 2016/0220743 A1* | 8/2016 | Guthrie | G06F 3/0482 |
| 2016/0228626 A1* | 8/2016 | Cassano | F21V 23/0464 |
| 2016/0296681 A1 | 10/2016 | Gaskin et al. | |
| 2018/0072553 A1* | 3/2018 | Lyons | B67D 1/0871 |

FOREIGN PATENT DOCUMENTS

| | | |
|---|---|---|
| EP | 1586340 A2 | 10/2005 |
| EP | 3533479 A1 | 9/2019 |
| EP | 3536359 A1 | 9/2019 |
| JP | H01132986 A | 5/1989 |
| JP | 2001-331223 A | 11/2001 |
| JP | 2015116431 A | 6/2015 |
| WO | WO-2014/161099 A1 | 10/2014 |
| WO | WO-2016/014469 A1 | 1/2016 |
| WO | WO-2018/054758 A1 | 3/2018 |

OTHER PUBLICATIONS

European Search Report for EPO Application No. 18189368, dated Oct. 12, 2018.
Taiwanese Second Office for Application No. 11020761140.
Australian Examination Report No. 1 for Application No. 2019322554, dated Aug. 2, 2021.
Australian Examination Report No. 3 for Application No. 2019322554, dated Apr. 13, 2022.
Australian Examination Report No. 2 for Application No. 2019322554, dated Dec. 20, 2021.
Notice of Reasons for Rejection for Japanese Patent Application No. 2021-507861, dated Apr. 21, 2022.
First Office Action for Korean Application No. 10-2021-7006223, dated Aug. 19, 2022.
First Office Action for Israel Patent Application No. 280888, dated Sep. 8, 2022.

* cited by examiner

FIG. 3
FIG. 2
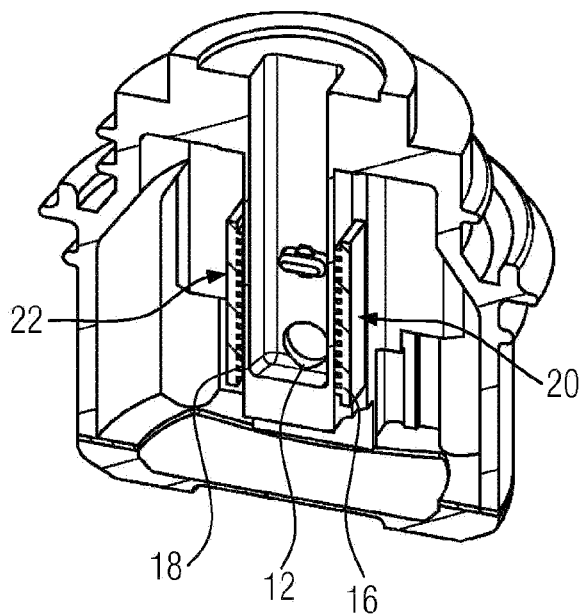
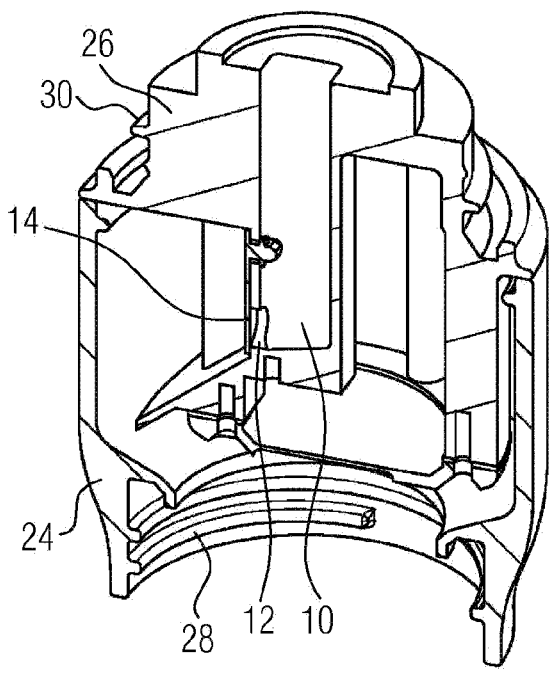
FIG. 4
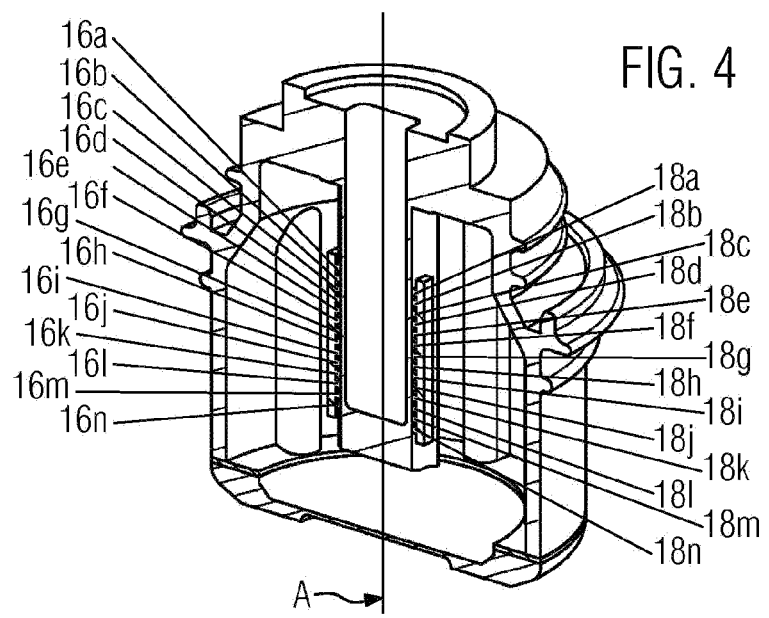

BABY BOTTLE WITH BOTTLE TOP ATTACHMENT

CROSS-REFERENCE TO RELATED APPLICATIONS

The present application is a continuation of U.S. patent application Ser. No. 17/232,648, filed Jan. 22, 2021, which is a US national phase of international patent application PCT/EP2019/071744, filed Aug. 13, 2019, and claims priority to European Patent Application EP 18189368.6, filed Aug. 16, 2018, the entirety of which are each hereby incorporated by reference.

BACKGROUND

An apparatus comprising a baby bottle and a bottle top attachment is known from US 2015/0283311 A1. The bottle top attachment is screwed onto the bottleneck of the baby bottle. In one embodiment, a sensor unit detects drops of milk dropping through the bottleneck of the baby bottle. In another embodiment, the open position of a flap valve disposed in the bottle neck is sensed. A conclusion can be drawn about the content of the baby bottle by determining the number of milk drops that reach the baby bottle or from the open position of the valve, respectively.

SUMMARY

This conclusion about the amount of milk is sometimes inaccurate, since the size and shape of the milk drops may vary. An object of the present invention is to improve the previously known apparatus. The present invention seeks, in particular, to provide an apparatus which allows for accurate and continuous detection of a parameter of the milk flowing into the baby bottle, is easy to clean, and ensures simple maintenance.

The apparatus comprises a baby bottle and a bottle top attachment coupled to the baby bottle. The bottle top attachment comprises a connector to which a breast pump can be connected. The breast pump typically comprises a breast shield that is adapted to the female human breast, and can in particular be sealingly applied thereto, and that is adapted to interact with a hand pump or an electrically operated pump to generate a negative pressure between the breast shield and the breast. The negative pressure is typically generated in a certain frequency corresponding to the pumping or suction strokes of the pump. This stimulates the milk flow. The connector typically comprises a channel which drains milk collected in the breast shield in the direction of a measuring head of the bottle top attachment. The breast shield can also be firmly integrated into the connector.

The bottle top attachment can be decoupled from the baby bottle, so that the filled baby bottle can be connected to a bottle nipple for feeding a baby. The bottle top attachment is releasably connected, typically screwed onto the bottleneck of the baby bottle. The apparatus according to the invention is characterized in that the bottle top attachment comprises a measuring head with a reservoir for breast milk and that the measuring head comprises a sensor unit associated with the volume of the reservoir. The sensor unit does not have to detect the entire volume of the reservoir.

The bottle top attachment is provided at an opening of the baby bottle which is typically formed by a bottleneck of the baby bottle. The bottle base is generally arranged on the end opposite the bottleneck. Usually, a baby bottle is designed such that it can stand freely and upright on the base of the bottle. Directional information such as top, bottom, vertical, horizontal, etc. in all cases relates to an apparatus standing with the bottle base on a flat, horizontal surface.

The baby bottle according to the invention is typically produced from at least partially transparent thermoplastic material or glass. Particularly preferably, polypropylene is used. The baby bottle made of plastic material can be produced as a disposable bottle or as a returnable bottle and usually has a weight of 7.5 to 30 g. The reusable baby bottle preferably has a wall thickness of about 0.9 mm.

The nominal volume of the baby bottle is typically 80 to 250 ml, in particular 80 ml, 150 ml or 250 ml. The maximum volume that the baby bottle can accommodate is usually no greater than 330 ml.

The baby bottle preferably has a height of about 60 to 160 mm, preferably 66 mm, 99.5 mm, 102 mm, 136 mm or 148.5 mm. The diameter of the bottle neck is typically 33 mm. The maximum diameter of the baby bottle is typically no greater than 50 to 70 mm, preferably no greater than 53 mm, 60 mm or 65 mm. All dimensions are to be understood having a tolerance of ±10%, preferably ±5%.

The baby bottle generally has a substantially cylindrical bottle body which tapers conically to form a bottleneck. The diameter of the body of the bottle can also vary over its length. For example, the body of the bottle can have several cylindrical sections of different diameters, which can in particular be connected by one or more conically shaped sections. The bottleneck usually has the smallest diameter. The bottleneck is preferably provided with an external thread.

The bottle base usually forms a bearing surface on which the baby bottle stands upright on a flat support surface. The bearing surface is typically a substantially flat surface which can optionally have a central curvature inwardly towards the reservoir. The footprint bearing surface can also be formed by a downwardly projecting ring.

The measuring head is typically arranged below the connector and captures in the reservoir the milk drops that were sucked into the connector preferably via a breast pump. For this purpose, the reservoir is typically formed having a filling opening at the upper end. Preferably, the reservoir is open toward the top. Furthermore, the reservoir is typically designed such that milk drops cannot drop directly through the reservoir. The lower side wall of the reservoir is preferably fluid-tight. The geometry of the reservoir defines a cavity that has a certain volume. This volume is typically between 0.5 ml and 4 ml, preferably 0.8 ml and 1.5 ml. This volume is associated with the sensor unit. In other words, the sensor unit is oriented toward the cavity of the reservoir. The sensor unit is in particular designed to determine a parameter of the milk in the reservoir, for example, the milk filling quantity in the reservoir.

The present invention enables determining a parameter of the milk before it enters the baby bottle. The accuracy is increased over prior art since the milk does not need to be measured when dropping and/or drop by drop. A plurality of milk drops can instead be combined to form a portion in the reservoir and is then measured or gauged by the sensor unit.

According to one preferred development of the present invention, the reservoir has an outflow opening to the baby bottle and a closure element arranged in the outflow opening. The closure element is there adapted such that it retains at least a certain amount of milk in the reservoir. The closure element is preferably designed as a valve which in a closed position bears against the outflow opening of the reservoir during a dropwise filling. If the fluid pressure in the reservoir exceeds a resistance threshold value of the closure element, then the closure element is forced to an open position, so that a certain amount of milk can flow out of the reservoir into the baby bottle. The closure element can be designed, for example, according to WO 2014/161099 A1 originating from the applicant, or in the manner of a flap valve according to US 2015/0283311 A1. Typically, the reservoir does not completely empty as a decrease in fluid pressure causes the closure member to return to the closed position.

The resistance threshold value of the closure element is preferably adjustable. The closure element is possibly pre-tensioned against the outflow opening. The filling height is preferably between 15 and 25 mm. The residual amount that typically remains in the reservoir after the closure element is again closed is typically 0.1 ml to 0.3 ml.

The fluid pressure of the milk in the reservoir acting upon the closure element is hydrostatic pressure. The valve is preferably designed as a one-way valve. Further preferably, the valve has a valve membrane which, due to its geometry, remains in the resting position during a fluid pressure on the valve membrane on the part of the baby bottle. In the resting position, the valve membrane rests against the outflow opening of the reservoir. The outflow opening is commonly provided on a side wall of the reservoir, so that the valve membrane is forced, preferably pivoted, away from the vertical to the open position. The valve membrane is preferably made of a flexible plastic material, in particular silicone.

A flow rhythm caused by the vacuum cycles of the pump, i.e. a portioned outflow of milk into the baby bottle can then be implemented in a simple and energy-saving manner.

According to one preferred development of the present invention, at least two optical sensor devices arranged opposite one another at the same height are associated with the reservoir. The terms "optical" and "light" in this context are not limited to visible light, but basically refer to the entire electromagnetic spectrum. The optical sensor devices are preferably adapted to the infrared range. In general, the sensor devices are arranged such that at least part of the milk column in the reservoir is provided between the sensor devices when milk fills the volume of the reservoir. The sensor devices are arranged to detect a differing signal, depending on whether milk or air is disposed between the sensor devices. The sensor devices are preferably integrated into oppositely disposed side walls of the reservoir, for example, by way of injection-molding. Alternatively, the sensor devices can each be mounted on the outer side of a transparent or translucent side wall on the reservoir.

It can then be determined whether a milk column in the reservoir extends between the sensor devices or how high it extends, so that a conclusion can be drawn about the milk filling quantity in the reservoir.

Further preferably, a light detector is arranged on one side of the reservoir and a light emitter on another side of the reservoir. The light detector and the light emitter are there arranged at the same height, so that the shortest light path between the light detector and the light emitter extends in the horizontal direction. The light emitter is typically oriented toward the light detector. The signal received by the light detector has a higher intensity when air is present between the light emitter and the light detector than when milk is present between the light emitter and the light detector.

The light emitter is preferably an LED or an LED chip and the light detector is preferably a phototransistor. Further preferably, several light detectors are arranged on one side of the reservoir and several light emitters on another side of the reservoir. The light detectors are arranged one above the other in the vertical direction. The same applies for the light emitters. Each light detector is associated with a light emitter arranged oppositely disposed at the same height. The light emitters and the light detectors are each preferably arranged in a straight line extending in the height direction.

The level of the milk column in the reservoir can then be determined more accurately.

According to one preferred development of the present invention, the apparatus comprises a control unit that is in a controlling manner connected to the light emitters and adapted such that the light emitters can be switched on and off again during a predetermined period of time and in a predetermined sequence. The period of time is usually a few milliseconds, preferably no more than 2 milliseconds. Since the period of time is selected to be very short, the milk column in the reservoir can be mapped at the respective point in time by plotting the measured intensity of the light detectors against the height of the respective light detectors. The sequence in which the light emitters are turned on and off again is usually less important, but is preferably sequential in the height direction.

The control unit preferably generates such a mapping at periodic intervals. According to this preferred development, the control unit is adapted such that switching the light emitter on and off repeats periodically. The period is preferably between 10 and 20 milliseconds, more preferably between 13 and 17 milliseconds, very preferably about 15 milliseconds.

This allows the level of the milk column in the reservoir to be monitored continuously.

According to one further preferred development of the present invention, the apparatus comprises a processing unit which is adapted to determine a parameter of the milk contained in the reservoir by way of a measured intensity of the light detectors. For example, the volume flow into the baby bottle can be calculated with the processing unit on the basis of the change in the milk level in the reservoir as a function of time. This allows for a direct conclusion regarding the milk delivery of the breast over time. Another parameter is the amount of milk in the reservoir at a given point in time, which can be determined by the current level of the milk column and the dimensions of the reservoir.

A central axis of the reservoir preferably coincides with a central axis of the measuring head. This allows the sensor unit to be optimally oriented to the reservoir. Furthermore, the control unit and the processing unit can be arranged between the reservoir and an outer wall of the measuring head.

More preferably, the reservoir has a substantially rectangular, in particular square cross-section. The cross-section there extends in the horizontal direction, so that the rectangular shape shows in a top view of the cross-section or of the reservoir, respectively. This simplifies the closure element bearing against the outflow opening, provided that the outflow opening is disposed on a side wall of the reservoir and the closure element is provided as a flat, plate-like element. The reservoir preferably has a length of 8 mm, a width of 8 mm and a height of 20 mm. The outlet opening preferably has a diameter of 5 mm.

According to one preferred development of the present invention, the measuring head comprises an outer housing and an inner housing forming the reservoir, where the outer housing is releasably connected to the inner housing. The inner housing is generally arranged coaxially in the outer housing.

This simplifies cleaning of the measuring head and maintenance of the sensor unit. The outer housing increases protection of the reservoir against impact and the sensor unit against damage.

The outer housing is preferably screwed by way of a thread onto the neck of the baby bottle. The bottle neck of the baby bottle generally has an external thread which interacts with an internal thread of the outer housing. Further preferably, the inner housing is screwed to the connector by way of a thread. The inner housing typically has an external thread circumferentially surrounded by the connector and in threaded engagement therewith.

As a result, the individual components of the bottle top attachment can be easily separated, so that cleaning and maintenance becomes easier.

The measuring head can alternatively be formed integrally and be releasably connected, preferably screwed, on the one side to the neck of the baby bottle and on the other side to the connector. According to a further alternative, the bottle top attachment can be formed entirely integrally.

The reservoir is preferably made of polypropylene (PP), where the reservoir should be permeable, in particular, to infrared light. The inner and the outer housings should also be made of polypropylene (PP).

In an independent aspect, the present invention provides a bottle top attachment for a baby bottle. It comprises a measuring head with a reservoir. The measuring head has a sensor unit associated with the volume of the reservoir. The bottle top attachment usually comprises a connector for a breast pump. The bottle top attachment is preferably formed according to one or more of the developments discussed above.

Further details of the present invention shall become apparent from the following description of an embodiment of the invention in combination with the drawing, in which:

BRIEF DESCRIPTION OF THE SEVERAL VIEWS OF THE DRAWING

FIG. 2 shows a sectional view of the measuring head of FIG. 1,

FIG. 3 shows a sectional view of the inner housing of the measuring head from FIG. 2 from a perspective rotated by 90° relative to FIG. 2, FIG. 4 shows a sectional view of the inner housing of the measuring head from a perspective rotated by 180° relative to FIG. 3.

DETAILED DESCRIPTION

Figure 1:
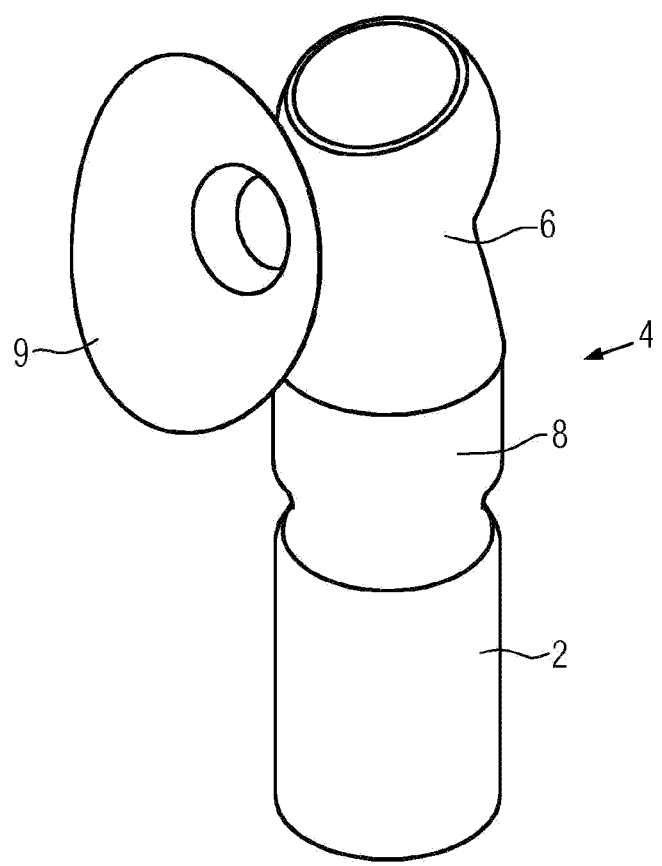
FIG. 1 shows a side view of an embodiment of the present invention.

FIG. 1 shows an embodiment of the apparatus according to the invention comprising a baby bottle 2 and a bottle top attachment 4 coupled to the baby bottle 2. The bottle top attachment 4 comprises a connector 6 and a measuring head 8 arranged between the baby bottle 2 and the connector 6. The measuring head 8 is screwed to the baby bottle 2 and the connector 6. The connector 6 typical has a connection for a breast pump. Only a breast shield 9 of this breast pump is shown in FIG. 1 and can be applied to a female breast and generate negative pressure on the breast in interaction with a pump connectable to the connector 6. According to this embodiment, the baby bottle 2 is rotationally symmetrical about a vertical axis of symmetry which coincides with a central axis of the measuring head. The baby bottle 2 is made of a transparent plastic material or glass.

FIG. 2 shows a sectional view of the measuring head 8, around the central axis A of which (see FIG. 4) a reservoir 10 is arranged. According to the embodiment, the reservoir 10 has a square cross-section. At the lower end of the side wall of the reservoir 10 in the figure at the left, the latter has an outflow opening 12. The lower base of the reservoir 10 is formed subsiding in the direction of the outlet opening 12. A closure element 14 bears against the outlet opening. The closure element 14 in the embodiment is formed as a valve membrane. With sufficient fluid pressure on the valve membrane by the milk in the reservoir, the valve membrane can lift laterally from the outlet opening 12 and expose it, at least in part. The outlet opening 12 is formed flush with the lowest point of the reservoir 10.

As shown in FIG. 3, light detectors 16 and light emitters 18 disposed opposite one another at the same height are associated with the reservoir. The light detectors 16 are arranged on one side 20 of the reservoir one above the other in a vertical line in the height direction. The light emitters 18 are correspondingly arranged one above the other on the opposite side 22 of the reservoir 10 in a vertical line in the height direction. The outlet opening can be seen in FIG. 3 as a substantially circular opening.

The measuring head 8 has an outer housing 24 and an inner housing 26 forming the reservoir 10 (see FIG. 2). The measuring head 8 is screwed with an external thread to the bottle neck of the baby bottle 2 by way of an internal thread 28 at the lower end of the outer housing 24. An external thread 30, with which the measuring head 8 is screwed to the connector 6, is formed on the inner housing 26 of the measuring head 8.

FIG. 4 illustrates the arrangement of the light detectors 16 and the light emitters 18 at equal heights on either side of the vertical axis of symmetry A of the measuring head 8. According to this embodiment, a total of 14 light detectors 16a to 16n and 14 light emitters 18a to 18n are provided. They are each arranged linearly one above the other in a vertical line parallel to the central axis A. The light detectors 16 and the light emitters 18 are each mounted in a side wall of the reservoir 10. The reservoir 10 is made of a transparent material.

Figure 5:
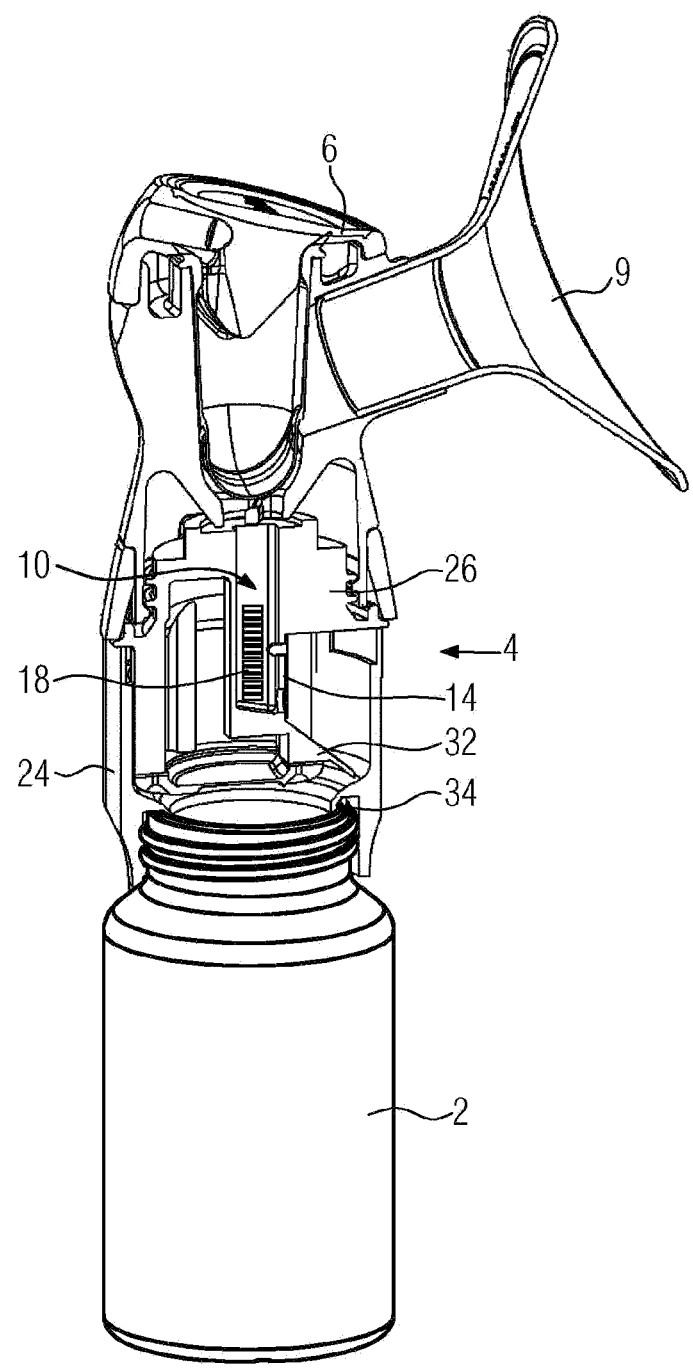
FIG. 5 shows a partial sectional view of the embodiment.

As shown in FIG. 5, the outlet opening 12 of the reservoir 10 is adjoined by a ramp 32 which slopes downwardly in the direction of the outer housing 24. The outer housing 24 has a collar 34 which surrounds the opening on the bottleneck and serves as a drip edge.

Breast milk collected in the breast shield 9 is passed into the connector 6 via a port integrally formed with the breast shield. The port extends from the breast shield 9 obliquely downwardly to the connector 6. A channel in the connector 6 is formed below the lower end of the port. The channel terminates directly above the upwardly open reservoir. Milk collected in the breast shield 9 flows into the reservoir 10 due to the geometry just described and gravity. The downwardly sloping base of the reservoir (see FIG. 2) causes the milk to first collect upstream of the outflow opening 12. The closure element 14 initially withstands the fluid pressure of the milk that results from a weight force. A milk column forms in the reservoir 10. If the fluid pressure of the milk column is large enough to force the closure element 14 away from the outflow opening 12, then a portion of the milk column can flow out of the reservoir 10 through the outflow opening 12. The portion there flows via the ramp 32 onto an inner wall of the outer housing. From this inner wall, the portion flows downwardly to the collar 34 where the portion finally drips into the baby bottle 2. If the closure element then moves to the closed position, the milk column in the reservoir rises again until the closure element is again forced to the open position.

According to the embodiment, the milk column in the reservoir 10 is transilluminated by the sensor devices 16, 18 every 15 ms. For this transillumination, the sensor devices 16, 18 need no more than 2 ms. Every 15 ms, a snapshot of the vertical extension of the milk column is created. The light detectors 16 arranged above the milk column measure a higher intensity than the light detectors 16 between which the milk column extends, since milk absorbs and/or scatters more light than air. The light detectors 16 and the light emitters 18 according to the embodiment, however, are adapted to the infrared range. The height of the milk column in the reservoir 10 is monitored continuously. With each open position of the closure element 14, the height of the milk column or the milk level, respectively, decreases. The amount of milk or the portion which flows into the baby bottle during one vacuum cycle of the suction pump can be calculated from this decrease. Since monitoring is continuous, the volume flow into the baby bottle, i.e. the amount of milk can be determined per unit time. If the volume flow is high, more milk is pumped out. If the volume flow is low, less milk is pumped out.

LIST OF REFERENCE NUMERALS

2 baby bottle
4 bottle top attachment
6 connector
8 measuring head
10 reservoir
12 outflow opening
14 closure element
16 light detector
18 light emitter
20, 22 oppositely disposed sides of the reservoir
24 outer housing
26 inner housing
28 internal thread
30 external thread
32 downwardly sloping ramp
34 drip edge
A central axis

What is claimed is:

1. An apparatus comprising:
 a baby bottle; and
 a bottle top attachment coupled to said baby bottle and having a connector for a breast pump; wherein
 said bottle top attachment comprises a measuring head with a reservoir for breast milk;
 said measuring head comprises an optical sensor unit configured to determine a current level of breast milk within said reservoir;
 said optical sensor unit is oriented towards a cavity of the reservoir, said reservoir comprising an outflow opening to said baby bottle; and
 light detectors of the optical sensor unit are arranged one above another in a height direction on one side of said reservoir and light emitters of the optical sensor unit are arranged one above another in the height direction on another side of said reservoir.

2. The apparatus according to claim 1, further comprising a closure element disposed in said outflow opening, said closure element being adapted such that it retains at least a certain amount of milk in said reservoir.

3. The apparatus according to claim 2, wherein the closure element is a valve that is arranged in said outflow opening, and in a closed position bears against said outflow opening of said reservoir and is forced to an open position due to a weight force of milk contained in said reservoir.

4. The apparatus according to claim 1, wherein each light detector on the one side of the reservoir is assigned to one light emitter arranged on the other side of the reservoir at the same height.

5. The apparatus according to claim 1, further comprising a control unit that is connected in a controlling manner to said light emitters and adapted such that said light emitters are switched on and off during a predetermined period of time and in a predetermined sequence.

6. The apparatus according to claim 5, wherein said control unit is adapted such that switching said light emitters on and off repeats periodically.

7. The apparatus according to claim 1, further comprising a processing unit which is adapted to determine a parameter of the milk contained in said reservoir by way of intensity measured by said light detectors.

8. The apparatus according to claim 1, wherein a central axis (A) of said reservoir coincides with a central axis (A) of said measuring head.

9. The apparatus according to claim 1, wherein said reservoir has a substantially rectangular cross-section.

10. The apparatus according to claim 1, wherein said measuring head comprises an outer housing and an inner housing forming said reservoir and said outer housing being releasably connected to said inner housing.

11. The apparatus according to claim 10, wherein said outer housing is screwed to a neck of said baby bottle by way of a thread.

12. The apparatus according to claim 10, wherein said inner housing is screwed to said connector by way of a thread.

13. The apparatus according to claim 1, wherein said reservoir has a substantially square cross-section.

* * * * *